United States Patent
Lin (10) Patent No.: US 11,254,706 B2
(45) Date of Patent: Feb. 22, 2022

(54) PEPTIDE AND ITS DERIVATIVES CAPABLE OF INHIBITING REPLICATION OF HEPATITIS V VIRUS IN HUMAN ADIPOSE-DERIVED STEM CELLS AND HEPATOCYTES

(71) Applicant: Inno Bio-Drug Development Limited, Tortola (VG)

(72) Inventor: Chen-Lung Lin, Taiwan (CN)

(73) Assignee: Inno Bio-Drug Development Limited, Tortola (VG)

(*) Notice: Subject to any disclaimer, the term of this patent is extended or adjusted under 35 U.S.C. 154(b) by 210 days.

(21) Appl. No.: 15/566,910

(22) PCT Filed: Apr. 16, 2015

(86) PCT No.: PCT/CN2015/076744

§ 371 (c)(1),
(2) Date: Oct. 16, 2017

(87) PCT Pub. No.: WO2016/165101

PCT Pub. Date: Oct. 20, 2016

(65) Prior Publication Data

US 2018/0134751 A1 May 17, 2018

(51) Int. Cl.

| | |
|---|---|
| *A61K 38/00* | (2006.01) |
| *A61K 38/10* | (2006.01) |
| *A61K 45/06* | (2006.01) |
| *A61P 31/14* | (2006.01) |
| *C07K 7/08* | (2006.01) |
| *C07K 14/81* | (2006.01) |
| *A61K 38/08* | (2019.01) |
| *C07K 7/06* | (2006.01) |

(52) U.S. Cl.

CPC ................ *C07K 7/08* (2013.01); *A61K 38/08* (2013.01); *A61K 38/10* (2013.01); *A61K 45/06* (2013.01); *A61P 31/14* (2018.01); *C07K 7/06* (2013.01); *C07K 14/8107* (2013.01); *A61K 38/00* (2013.01); *C12N 2770/24211* (2013.01)

(58) Field of Classification Search

None

See application file for complete search history.

(56) References Cited

U.S. PATENT DOCUMENTS

2012/0135931 A1 5/2012 Kini et al.

FOREIGN PATENT DOCUMENTS

| | | | |
|---|---|---|---|
| CN | 104321337 A | | 1/2015 |
| WO | 2006/130553 A2 | | 12/2006 |
| WO | 2007/097492 A1 | | 8/2007 |
| WO | 2013/173941 A1 | | 11/2013 |
| WO | WO 2013/173941 | * | 11/2013 |

OTHER PUBLICATIONS

Borigini (The Hepatitis-Fibromyalgia Connection, Oct. 9, 2012) (Year: 2012).*

Hepatitis C, downloaded on Dec. 13, 2019 from URL:< https://www.sfcdcp.org/infectious-diseases-a-to-z/hepatitis-c/>) (Year: 2019).*

"Biology online" (downloaded on Aug. 17, 2020 from URL:<https://www.biologyonline.com/dictionary/inhibit>) (Year: 2020).*

Bartenschlager, Ralf, and Lohmann, Volker, "Novel cell culture systems for the hepatitis C virus," Antiviral Research, 2001, vol. 52, pp. 1-17.

Bhogal, Ricky H., et al., "Isolation of Primary Human Hepatocytes from Normal and Diseased Liver Tissue: A One Hundred Liver Experience," PLoS ONE, Mar. 2011, vol. 6, Issue 3, e18222, pp. 1-8.

Dorner, Marcus, et al., "A genetically humanized mouse model for hepatitis C virus infection," Nature, Jun. 9, 2011, vol. 474, pp. 208-211.

Fletcher, Nicola F., et al., "Hepatitis C Virus Infection of Neuroepithelioma Cell Lines," Gastroenterology, Oct. 2010, vol. 139, No. 4, pp. 1365-1374.

Lin, Chen-Lung, et al., "Immunization with Epstein-Barr Virus (EBV) Peptide-pulsed Dendritic Cells Induces Functional CD8+ T-Cell Immunity and May Lead to Tumor Regression in Patients with EBV-positive Nasopharyngeal Carcinoma," Cancer Research, Dec. 1, 2002, vol. 62, pp. 6952-6958.

Lindenbach, Brett D., and Rice, Charles M., "Unravelling hepatitis C virus replication from genome to function," Nature, Aug. 18, 2005, vol. 436, pp. 933-938.

Mercer, David F., et al., "Hepatitis C virus replication in mice with chimeric human livers," Nature Medicine, Aug. 2001, vol. 7, No. 8, pp. 927-933.

Scheel, Troels K. H., and Rice, Charles M., "Understanding the hepatitis C virus life cycle paves the way for highly effective therapies," Nature Medicine, Jul. 2013, vol. 19, No. 7, pp. 837-849.

Sheehy, P., et al., "In vitro replication models for the hepatitis C virus," Journal of Viral Hepatitis, 2007, vol. 14, pp. 2-10.

Sheets, W.F., "Hepatitis C," World Health Organization, Media Centre, Fact Sheet No. 164, Jul. 2012. Retrieved from the Internet: <URL: http://www.who.int/mediacentre/factsheets/fs164/en/>, 4 pages.

Wang, Alice, et al., "Site-Specific Mutagenesis of the Human Interleukin-2 Gene: Structure-Function Analysis of the Cysteine Residues," Science, Jun. 29, 1984, vol. 224, pp. 1431-1433.

(Continued)

*Primary Examiner* — Sergio Coffa

(74) *Attorney, Agent, or Firm* — Fitch, Even, Tabin & Flannery, LLP

(57) ABSTRACT

Hepatitis C virus (HCV) infection is a leading cause for liver cirrhosis and hepatocellular carcinoma worldwide[2]. Current therapeutic regimens are usually poorly tolerated and only effective in a proportion of infected individuals. We discovered a peptide with sequence of DEAQETAVSSHEQD (SEQ ID NO: 1), a fragment of rabbit $\alpha$1-antiproteinase F, and its derivatives DEAQETAVSSHEQ (SEQ ID NO: 2) and QETAVSSHEQD (SEQ ID NO: 3), significantly inhibit serum-borne HCV replication in hADSC and human hepatocytes.

7 Claims, 2 Drawing Sheets

Specification includes a Sequence Listing.

(56) References Cited

OTHER PUBLICATIONS

Wilson, Garrick K., and Stamataki, Zania, "In Vitro Systems for the Study of Hepatitis C Virus Infection," International Journal of Hepatology, 2012, vol. 2012, Article ID 292591, 8 pages.
Patent Cooperation Treaty, International Search Report for International Application No. PCT/CN2015/076744 dated Jan. 18, 2016, 6 pages.
Patent Cooperation Treaty, Written Opinion of the International Searching Authority for International Application No. PCT/CN2015/076744 dated Jan. 18, 2016, 4 pages.
European Patent Office, Extended European Search Report dated Oct. 12, 2018 for European Patent Application No. 15 888 806.5, 7 pages.

\* cited by examiner

SEQUENCE LISTING

```
<160> NUMBER OF SEQ ID NOS: 4

<210> SEQ ID NO 1
<211> LENGTH: 14
<212> TYPE: PRT
<213> ORGANISM: Oryctolagus cuniculus
<220> FEATURE:
<221> NAME/KEY: MISC_FEATURE
<222> LOCATION: (1)..(14)
<223> OTHER INFORMATION: residues 1-14 of rabbit alpha1-antiproteinase F

<400> SEQUENCE: 1

Asp Glu Ala Gln Glu Thr Ala Val Ser Ser His Glu Gln Asp
1               5                   10

<210> SEQ ID NO 2
<211> LENGTH: 13
<212> TYPE: PRT
<213> ORGANISM: Artificial Sequence
<220> FEATURE:
<223> OTHER INFORMATION: A derivative of DEA

<400> SEQUENCE: 2

Asp Glu Ala Gln Glu Thr Ala Val Ser Ser His Glu Gln
1               5                   10

<210> SEQ ID NO 3
<211> LENGTH: 11
<212> TYPE: PRT
<213> ORGANISM: Artificial Sequence
<220> FEATURE:
<223> OTHER INFORMATION: A derivative of DEA
```

-continued

```
<400> SEQUENCE: 3

Gln Glu Thr Ala Val Ser Ser His Glu Gln Asp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: HLA-A11 restricted, Epstein-Barr virus-specific
      peptide epitope

<400> SEQUENCE: 4

Cys Ser Ser Cys Ser Ser Cys Pro Leu Ser Lys
1               5                   10
```

PEPTIDE AND ITS DERIVATIVES CAPABLE OF INHIBITING REPLICATION OF HEPATITIS V VIRUS IN HUMAN ADIPOSE-DERIVED STEM CELLS AND HEPATOCYTES

CROSS-REFERENCE TO RELATED APPLICATION

This application is a U.S. national phase application filed under 35 U.S.C. § 371 of International Application Number PCT/CN2015/076744, filed Apr. 16, 2015, designating the United States.

REFERENCE TO A SEQUENCE LISTING

The Sequence Listing associated with this application is filed in electronic format via EFS-Web and is hereby incorporated into the specification in its entirety. The name of the text file containing the Sequence Listing is "FPCH13160112_SEQUENCE LISTING." The size of the text file is 1.28 KB, and the text file was created on Sep. 29, 2017.

FIELD OF THE INVENTION

The present invention relates to a peptide and its derivatives capable of inhibiting replication of hepatitis C virus, its encoding polynucleotide, a vector, a host cell and a pharmaceutical composition comprising said peptide, and uses thereof.

BACKGROUND OF THE INVENTION

HCV is an enveloped positive-strand RNA virus in the Flaviviridae family. It contains a 9.6 kb genome starting at a untranslated region (5'-UTR), followed by sequences encoding structural proteins (core, E1, and E2) and non-structural (NS) proteins including p7, NS2, NS3, NS4A and 4B, NS5A and 5B (for review, ref[1]). At least 170 million people are chronically infected by HCV, resulting in death of more than 350,000 people annually[2]. Current treatment such as combinatorial use of PEG-interferon and antiviral drug ribavirin, has many side effects and is effective in only a proportion of infected patients. Development of new anti-HCV therapeutics has been rigorously attempted (for review, ref[3]), for which, however, the lack of a reliable and physiological cell culture system to grow serum-borne HCV (HCVser) still remains an obstacle. For example, direct infection of HCVser was only demonstrated in primary human and chimpanzee hepatocytes, and the infection was transient and inefficient[4]. Recently devised in vitro cell-based culture methods employ molecular clones of HCV genomes, not natural virus (for review, ref[5]). In addition, these models propagated HCV in non-primary human cells such as hepatoma cell lines[6] or neuroepithelial cell lines[7]. Hence, there are concerns over extrapolating findings into the clinical virus-host interaction. Animal models such as chimpanzees, human-liver chimeric mice[8] or genetically modified mice susceptible to HCV infection[9] are difficult to access or establish. To overcome this, in the co-pending application (PCT/CN2015/070243), we successfully developed a platform in which a subset of human adipose-derived stem cells (hADSC) support complete replication of serum-derived HCV genotype 1a, 1b, 2a, 2b and mixed 2a+2b. Furthermore, newly produced viruses are infectious to naïve hADSC, and serial "re-infection" to naïve hADSC maintains viral replication and the total viral titer can be escalated to more than $1\times10^{11}$ copies after 6 cycles of re-infection. Of significance, viruses produced by serum-borne HCV infected hADSC were infectious to primary human hepatocytes.

There still remains a need for effective drugs and treatment with fewer side effects. Progresses in devising small molecules as new generations of anti-HCV treatment have been made recently; however, production of these HCV-specific enzyme inhibitors is costly. Moreover, its long-term adverse effects require further monitoring. Thus, novel anti-HCV therapies composed of or derived from natural products, which conceivably will lead to a safer profile, and come with a lower production cost still need to be developed.

SUMMARY OF THE INVENTION

This Summary is provided to present a summary of the invention to briefly indicate the nature and substance of the invention. It is submitted with the understanding that it will not be used to interpret or limit the scope or meaning of the claims.

In one aspect, the present disclosure provides a method for treating or preventing HCV infection, or inhibiting the replication of HCV in a subject, wherein the method comprises administrating to the subject of an effective amount of a peptide comprising an amino acid sequence having at least 70% identity to the amino acid sequence DEAQETAVSSHEQD (SEQ ID NO: 1) or variants, derivatives, mutants, or fragments thereof. In some embodiments, the amino acid sequence of the peptide has the amino acid sequence of at least 75%, 80%, 85%, 90%, 95%, 98% or 99% or more identity to the amino acid sequence DEAQETAVSSHEQD (SEQ ID NO: 1). In some embodiments, the peptide comprises the amino acid sequence DEAQETAVSSHEQD (SEQ ID NO: 1), QETAVSSHEQD (SEQ ID NO: 3), or DEAQETAVSSHEQ (SEQ ID NO: 2). In some embodiments, the sequence of the peptide is substantially consisted of, or consisted of DEAQETAVSSHEQD (SEQ ID NO: 1), QETAVSSHEQD (SEQ ID NO: 3), or DEAQETAVSSHEQ (SEQ ID NO: 2). In some embodiments, the peptide comprises at least one amino acid addition, deletion, and/or substitution. In some embodiments, the amino acid addition, deletion and/or substitution are performed at the C-terminal and/or N-terminal. In some embodiments, the peptide has 1-5, preferably 1-3 amino acid additions, deletions, and/or substitutions. In some embodiments, the method further comprises administrating another anti-HCV agent. Such anti-HCV agent can be administrated prior to, after or simultaneously with the peptide of the invention. In some embodiments, HCV is of genotype 1a, 1b, 2a, or 2b, or genotype 3, or genotype 4.

In another aspect, the present disclosure provides a peptide, comprising an amino acid sequence having at least 70% identity to the amino acid sequence QETAVSSHEQD (SEQ ID NO: 3), or DEAQETAVSSHEQ (SEQ ID NO: 2), or variants, derivatives, mutants, or fragments thereof. In some embodiments, the amino acid sequence of the peptide has at least 75%, 80%, 85%, 90%, 95%, 98% or 99% or more identity to the amino acid sequence QETAVSSHEQD (SEQ ID NO: 3), or DEAQETAVSSHEQ (SEQ ID NO: 2). In some embodiments, the peptide comprises, is substantially consisted of, or is consisted of, the amino acid sequence QETAVSSHEQD (SEQ ID NO: 3), or DEAQETAVSSHEQ (SEQ ID NO: 2). In some embodiments, the peptide comprises at least one amino acid addition, deletion, and/or substitution. In some embodiments, the amino acid addition, deletion and/or substitution are performed at the C-terminal and/or N-terminal. In some embodiments, the peptide has 1-5, preferably 1-3 amino acid additions, deletions, and/or substitutions. In some embodiments, the peptide has inhibitory effects over the HCV replication. In some embodiments, the peptide is isolated, or is obtained by chemical synthesis.

In another aspect, the present disclosure provides a polynucleotide which encodes the peptide of the present invention.

In another aspect, the present disclosure provides a vector comprises the polynucleotide of the present invention.

In another aspect, the present disclosure provides a host cell which comprises the polynucleotide or vector of the present invention.

In another aspect, the present disclosure provides a pharmaceutical composition comprising an efficient amount of the peptide, polynucleotide, vector, or host cell of the present invention, and a pharmaceutically acceptable carrier.

In another aspect, the present disclosure provides use of the peptide, polynucleotide, vector, host cell, or pharmaceutical composition of the present invention in the manufacture of a medicament for treating or preventing HCV infection, or inhibiting the replication of HCV in a subject. In some embodiments, the medicament further comprises another anti-HCV agent. In some embodiments, HCV is of genotype 1a, 1b, 2a, or 2b, or genotype 3, or genotype 4.

Other aspects are described infra.

BRIEF DESCRIPTION OF THE DRAWINGS

The foregoing summary and detailed description is better understood when read in conjunction with the accompanying drawings which are included by way of example and not by way of limitation.

FIG. 1. DEAQETAVSSHEQD (SEQ ID NO: 1) and its derivatives effectively inhibit the replication of serum-borne HCV in hADSC and primary hepatocytes. (A and B) Concentrations of 1, 10 and 100 µg/ml of DEA, DEA-Q and QET peptides were added into the culture of p5 hADSC for 1 h before exposure to HCV(+) serum (genotype 1b). HLA-A11 restricted, Epstein-Barr virus-specific peptide epitope CSSCSSCPLSK was used as a control (irrelevant) peptide. On day 21 post-infection, the 5'-UTR copy numbers in the supernatant (A) and cell lysates (B) were quantified by qRT-PCR. Data are expressed as mean±SD from 3 experiments. (C) Concentrations of 1, 10 and 100 µg/ml of DEA, DEA-Q and QET peptides were added into the culture of primary human hepatocytes 1 h before exposure to HCVser (genotype 1b). Five days post-infection, the cellular RNAs were extracted for RT-PCR of 5'-UTR. Data are expressed as mean±SD from 3 experiments. HCV copy numbers for DEA, DEA-Q and QET at some concentrations (such as 10 and 100 µg/ml) are under detection limit.

DETAILED DESCRIPTION OF THE EMBODIMENTS OF THE INVENTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

As used herein, the singular forms "a", "an" and "the" are intended to include the plural forms as well, unless the context clearly indicates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The peptide of the disclosure may be a recombinant, natural, or synthetic peptide. The peptide of the disclosure may be a purified natural product or a chemically synthetic product. Alternatively, it may be produced from prokaryotic or eukaryotic hosts, such as bacteria, yeast, higher plant, insect, and mammalian cells, using recombinant techniques. According to the host used in the recombinant production, the peptide may be glycosylated or non-glycosylated. In one embodiment, the peptide of the disclosure is derived from a fragment of rabbit α1-antiproteinase F, and its derivatives.

As used herein, the terms "derivative", "variant", "mutants" and "fragment" mean the peptide that essentially retains the same biological functions or activity of the present peptide.

As used herein, the term "derivative" includes, but is not limited to, (i) one in which one or more of the amino acid residues include a substituent group, (ii) one in which the peptide is fused with another compound, such as a compound to increase the half-life of the peptide (for example, polyethylene glycol), (iii) one in which the additional amino acids are fused to the peptide, such as a leader or secretary sequence or a sequence used for purifying peptide or pro-protein, or (iv) one in which the peptide is modified by some modifications. Such derivatives are known to the artisans based on the teachings herein.

As used herein, the term "modification" (which does not normally alter primary sequence) includes in vivo or in vitro chemical derivation of peptides, e.g., acelylation, or carboxylation. Also included are modifications of glycosylation, e.g., those made by modifying the glycosylation patterns of a peptide during its synthesis and processing or in the further processing steps, e.g., by exposing the peptide to glycosylation enzymes (e.g., mammalian glycosylating or deglycosylating enzymes). Also included are sequences having phosphorylated amino acid residues, e.g., phosphotyrosine, phosphoserine, phosphothronine, as well as sequences modified to improve the resistance to proteolytic degradation or to optimize solubility properties.

As used herein, the term "variant" includes, but is not limited to, deletions, insertions and/or substitutions of several amino acids, preferably several conserved amino acid substitutions (typically 1-7, preferably 1-6, more preferably 1-5, even more preferably 1-4, still more preferably 1-3, most preferably 1-2), and addition of one or more amino acids (typically less than 20, preferably less than 10, more preferably less than 5) at C-terminal, N-terminal or inside the peptide. For example, the protein functions are usually unchanged when an amino residue is substituted by a similar or analogous one, e.g. substituted with a conserved or non-conserved amino acid residue (preferably a conserved amino acid residue). Further, the addition of one or several amino acids at C-terminal and/or N-terminal usually does not change the protein function.

As used herein, "conserved amino acid substitutions" means a peptide formed by substituting at most 7, preferably at most 6, more preferably 5, and most preferably at most 3 amino acids with the amino acids having substantially the same or similar property, as compared with the original amino acid sequence. Naturally-occurring amino acids can be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions can involve exchange of a member of one of these classes with another member of the same class. Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

Exemplary conservative amino acid substitutions are set forth in Table 1.

TABLE 1

Conservative Amino Acid Substitutions

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

A skilled artisan will be able to determine suitable variants of polypeptides as set forth herein using well-known techniques coupled with the information provided herein. One skilled in the art can identify suitable areas of the molecule that can be changed without destroying activity by targeting regions not believed to be important for activity. The skilled artisan also will be able to identify residues and portions of the molecules that are conserved among similar polypeptides. In further embodiments, even areas that can be important for biological activity or for structure can be subject to conservative amino acid substitutions without destroying the biological activity or without adversely affecting the peptide structure.

The polynucleotide of invention may be in the forms of DNA and RNA. DNA includes cDNA, genomic DNA, and synthetic DNA, etc., in single strand or double strand form. The polynucleotide of invention may be a degenerate sequence. As used herein, the term "degenerate sequence" means that there are different sequences which encode the same protein due to the degeneracy of codons.

The term "polynucleotide encoding the peptide" includes the polynucleotide encoding said peptide and the polynucleotide comprising additional and/or non-encoding sequence.

The polynucleotide encoding the peptide herein can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. Once the sequence is obtained, one can produce lots of the sequences by recombinant methods. Usually, said sequence is cloned into a vector which is then transformed into a host cell. The sequence is isolated from the amplified host cells using conventional techniques.

The invention further relates to a vector comprising the polynucleotide of the disclosure, a genetic engineered host cell transformed with the vector or the polynucleotide of the disclosure, and the method for producing the peptide by recombinant techniques.

The recombinant peptides can be expressed or produced by the conventional recombinant DNA technology (Science, 1984; 224:1431), using the polynucleotide sequence of invention. Generally, it comprises the following steps:
(1) transfecting or transforming the appropriate host cells with the polynucleotide encoding the peptide or the vector containing the polynucleotide;
(2) culturing the host cells in an appropriate medium;
(3) isolating or purifying the protein from the medium or cells.

In the invention, the polynucleotide sequences herein may be inserted into a recombinant expression vector. The term "expression vector" means a bacterial plasmid, bacteriophage, yeast plasmid, plant virus or mammalian cell virus, such as adenovirus, retrovirus or any other vehicles known in the art. Any plasmid or vector can be used to construct the recombinant expression vector as long as it can replicate and is stable in the host. One important feature of expression vector is that the expression vector typically contains a replication origin, a promoter, a marker gene as well as the translation regulatory components.

The known methods can be used to construct an expression vector containing the sequence herein and appropriate transcription/translation regulatory components. These methods include in vitro recombinant DNA technique, DNA synthesis technique, in vivo recombinant technique, etc. The DNA sequence is efficiently linked to the proper promoter in an expression vector to direct the synthesis of mRNA. The exemplary promoters are lac or trp promoter of *E. coli*; PL promoter of λ phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

As used herein, the "host cell" includes prokaryote, e.g., bacteria; primary eukaryote, e.g., yeast; advanced eukaryotic, e.g., mammalian cells. The representative examples are bacterial cells, e.g., *E. coli, Streptomyces, Salmonella typhimurium*; fungal cells, e.g., yeast; plant cells; insect cells e.g., *Drosophila* S2 or Sf9; animal cells e.g., CHO, COS or Bowes melanoma, etc.

The invention further relates to a method for treating or preventing HCV infection, or inhibiting the replication of HCV in a subject, comprising administrating to the subject of an effective amount of the peptide of the invention. Such peptide can include, but is not limited to, a peptide comprising an amino acid sequence having at least 70% identity to the amino acid sequence DEAQETAVSSHEQD (SEQ ID NO: 1) or variants, derivatives, mutants, or fragments thereof. In an embodiment, the peptide comprises, is substantially consisted of, or is consisted of the amino acid sequence DEAQETAVSSHEQD (SEQ ID NO: 1), QETAVSSHEQD (SEQ ID NO: 3), or DEAQETAVSSHEQ (SEQ ID NO: 2). In an embodiment, the peptide can be a variant, derivative, mutant, or fragment of the peptide DEAQETAVSSHEQD (SEQ ID NO: 1), QETAVSSHEQD (SEQ ID NO: 3), or DEAQETAVSSHEQ (SEQ ID NO: 2), as long as said variant, derivative, mutant, or fragment retains the inhibiting effect on HCV of the peptide DEAQETAVSSHEQD (SEQ ID NO: 1), QETAVSSHEQD (SEQ ID NO: 3), or DEAQETAVSSHEQ (SEQ ID NO: 2). For example, the inhibiting effect on HCV of said variant, derivative, mutant, or fragment can be at least 40%, 50%, 60%, 70%, 80%, 90%, 100%, 110% or more of the inhibiting effect on HCV of the peptide DEAQETAVSSHEQD (SEQ ID NO: 1), QETAVSSHEQD (SEQ ID NO: 3), or DEAQETAVSSHEQ (SEQ ID NO: 2). Skilled persons in the art can routinely select and determine such variant, derivative, mutant, and fragment.

The term "an effective amount," as used herein, refers to the amount of an active component that is sufficient to show a meaningful patient benefit, e.g., a sustained reduction in viral load.

HCV according to the invention can be any HCV that can infect hADSCs or human hepatocytes, or any HCV that can be separated from HCV infected individuals. In one embodiment, HCV is at least one of the HCV genotypes selected from the group consisting of genotypes 1a, 1b, 2a, 2b, 2c, 2d, 3a, 3b, 3c, 3d, 3e, 3f, 4a, 4b, 4c, 4d, 4e, 4f, 4g, 4 h, 4i, 4j, 5a and 6a, or any combination thereof. In another embodiment, HCV is at least one of the HCV genotypes selected from the group consisting of genotypes 1a, 1b, 2a, 2b, 3, and 4.

The level of HCV can be determined by any known technique in the art. Such techniques may include anti-HCV ELISA assay (Enzyme Linked ImmunoSorbent Assay), which tests for HCV proteins. Testing for HCV replication by amplification tests RNA (e.g. polymerase chain reaction or PCR, branched DNA assay) may be used. The synthesis of the RNAs of the HCV may be indeed analysed by RT-PCR in a single step using a device designed for real time PCR or by hybridization of the RNAs on filters using HCV-specific radioactive probes. For instance, the isolated RNA may be subjected to coupled reverse transcription and amplification, such as reverse transcription and amplification by polymerase chain reaction (RT-PCR), using specific oligonucleotide primers that enable amplification of HCV genome. Then a direct sequencing may be performed to determine the genotype of HCV that has infected said subject.

As used herein, the term "Human Adipose-Derived Stem Cell" (hADSC) is a human adult stem cell that is or has a parental cell that was obtained from a tissue source containing adipose tissue. In some cases, hADSC is also referred to as stromal vascular fraction (SVF), which is the very origin of the series of ADSCs. SVF is the primary cells isolated from human adipose tissues, and in culture they will proliferate (increase in cell number) spontaneously.

As used herein, the terms "patient," "subject," "individual," and the like are used interchangeably, and refer to any animal amenable to the methods described herein, and include human, non-human mammalians (for example, cow, sheep, rabbit, dog, mouse, rat, monkey, etc.) and domestic poultry.

The invention also provides a pharmaceutical composition comprising an effective amount of the peptide herein, its variant, derivative, mutants and/or fragments in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 µg-50 mg/kg body weight or more per day.

Moreover, the peptide of the present disclosure can be administered with other anti-HCV agents in combination therapy, either jointly or separately, or by combining the compounds into a composition. Agents that can be administered with the peptides of this disclosure include, but are not limited to, an interferon and a ribavirin, boceprevir, telaprevirs, or sofosbuvir. The interferon can be selected from interferon alpha 2B, pegylated interferon alpha, consensus interferon, interferon alpha 2A, interferon lambda, pegylated interferon lambda, and lymphoblastoid interferon tau.

The peptide of the present disclosure may also be used as a laboratory reagent. The peptide may be useful in providing research tools for designing of viral replication assays, validation of animal assay systems and structural biology studies to further enhance knowledge of the HCV disease mechanisms. Further, the peptide of the present disclosure is useful in establishing or determining the binding site of other antiviral agents, for example, by competitive inhibition.

The peptide of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The embodiments of the peptides, pharmaceutical compositions, uses and methods of the present disclosure are intended to be illustrative and not limiting. Modifications and variations can be made by the skills in the art in light of the above teachings, specifically those that may pertain to alterations in the peptides maintaining near native functionally with respect to anti-HCV virus effect. Therefore, it should be understood that changes may be made in the particular embodiments disclosed which are within the scope of what is described.

The invention is further illustrated by the following examples. These examples are only intended to illustrate the invention, but not to limit the scope of the invention. For the experimental methods in the following examples, they were performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

Example 1

Peptide Preparation

General information for synthesis. Amino acids used for the synthesis: Fmoc-Ala-OH, Fmoc-Asp(tBu)-OH, Fmoc-Gln(Trt)-OH, Fmoc-Glu(tBu)-OH, Fmoc-His(Trt)-OH, Fmoc-Ser(tBu)-OH, Fmoc-Thr(tBu)-OH, Fmoc-Val-OH. HPLC analysis was performed on Agilent 1100 seriers system using C18 column (BIOSIL, 4.6 mm×150 mm, 5 □μm). Detection is by UV at 220 nm. The flow rate is 0.3 mL/min. For peptide-3 and 5, the following gradient elution (solvent A: 0.1% TFA/$H_2O$, solvent B: 0.1% TFA/MeOH) is used: 100% A at 0 min, 80% A, 20% B at 10 min, 50% A, 50% B at 15 min, 100% B at 20 min, and 100% B for additional 10 min. Mobile phase for QET in HPLC (NUCLEODUR C18 Pyramid, 4.6 mm×250 mm, 5 □μm) is 0.1% TFA/$CH_3OH$. MALDI-TOF mass spectrometer (Autoflex III system, BrukerDaltonics) and Nuclear Magnetic Resonance spectroscopy (Varian Unity Plus 400 MHz) are used for peptide identification.

General synthesis and purification of peptides. Peptides were synthesized using standard Fmoc-strategy with a Solid Phase Peptide Synthesizer (PS3). Generally, D or Q residue preloaded Wang resin (0.79 mmol/g load) was weighed into the reaction vessel and swelled with freshly DMF (5 mL) for 1 hr prior to synthesis. The first and the sequential Fmoc groups were removed with 20% piperidine in 5 mL DMF (as "DEP" solution) for 5 min twice to free amine on N-terminus. Thereafter, 0.4 MN-methylmorpholine in 3 mL DMF was added for C-terminal activation (as "ACT") and the desired amino acids (as Fmoc-AA(protected side chain)-OH) and PyBOP were used in four-fold excess for coupling (called AA). After "AA" proceeding for proper time (see Table 2), N terminal amino acid was introduced $Ac_2O$ (100 □μL) to cap the rest of unreacted free amine (called CAP) in ACT solution for 25 min (as CAP). Then, keep repeating DEP-ACT-AA-CAP cycles to construct the peptides from C to N terminus. All reactions were monitored by Kaisar test. Finally, peptides were removed from the solid support by treat with 95% TFA/$H_2O$ in ice bath and return to room temperature for 1.5 hours. The crude product was collected by filtration. The crude was purified by medium pressure liquid chromatography using C18 column (MERCK Lobar 310-25 Lichrprep). The purity was identified by HPLC system. The synthesized peptides were characterized by MALDI-TOF mass spectrometer and Nuclear Magnetic Resonance spectroscopy.

Results

Peptide-3 (DEA-Q): DEAQETAVSSHEQ (SEQ ID NO: 2), yield: 29%. Retention time: 17.7 min (purity>95%). MS (MALDI-TOF): Calcd: 1430 Da (M+H$^+$), found: 1430 Da (M+H$^+$) (observed). $^1$H-NMR (400 MHz, $D_2O$): □8.54 (s, 1H), 7.22 (s, 1H), 4.65 (m, 1H), 4.51 (q, J=7 Hz, 1H), 4.30 (m, 8H), 4.09 (m, 3H), 3.77 (m, 3H), 3.58 (m, 2H), 3.23 (dd, J=6 and 6 Hz, 1H), 3.09 (dd, J=8 and 9 Hz, 1H), 2.97 (dd, J=5 and 5 Hz, 1H), 2.87 (dd, J=8 and 8 Hz, 1H), 2.42 (m, 6H), 2.04 (m, 15H), 1.30 (t, J=7 Hz, 6H), 1.16 (m, 3H), 0.87 (dd, J=4 and 4 Hz, 6H).

Peptide-5 (DEA): DEAQETAVSSHEQD (SEQ ID NO: 1), yield: 28%. Retention time: 16.5 min (purity>95%). MS (MALDI-TOF):Calcd: 1545 Da. (M+H$^+$), found: 1545 Da ((M+H$^+$). $^1$H-NMR (400 MHz, $D_2O$): □8.53 (s, 1H), 7.20 (s, 1H), 4.64 (m, 2H), 4.50 (t, J=7 Hz, 1H), 4.30 (m, 8H), 4.08 (m, 3H), 3.69 (m, 5H), 3.20 (dd, J=6 and 6 Hz, 1H), 3.07 (dd, J=8 and 8 Hz, 1H), 2.85 (m, 3H), 2.42 (m, 6H), 2.07 (m, 15H), 1.28 (m, 6H), 1.15 (m, 3H), 0.86 (dd, J=3 and 3 Hz, 6H).

QET: QETAVSSHEQD (SEQ ID NO: 3); retention time: 3.9; MS (MALDI-TOF): Calcd.:1230 Da ([M+H]), found: 1230. Da ([M+H]).

TABLE 2

The reaction time for each amino acid coupling (AA).

| Residue No. ## | Peptide-3 (DEA-Q) | Peptide-5 (DEA) Reacting time # | QET |
|---|---|---|---|
| 1 | 1 hr*1 | 1 hr*2 | 5 hr*2 |
| 2 | 2 hr*1 | 2 hr*2 | 6 hr*2 |
| 3 | 1 hr*1 | 2 hr*1 | 5 hr*1 |
| 4 | 2 hr*1 | 2 hr*1 | 5 hr*1 |
| 5 | 1.5 hr*1 | 2 hr*2 | 6 hr*1 |
| 6 | 2 hr*1 | 1.5 hr*2 | 6 hr*1 |
| 7 | 2 hr*1 | 2 hr*1 | 6 hr*1 |
| 8 | 2 hr*1 | 2 hr*1 | 6 hr*3 |
| 9 | 2.5 hr*1 | 2 hr*2 | 6 hr*2 |
| 10 | 2 hr*1 | 2.5 hr*2 | 6 hr*1 |
| 11 | 2 hr*1 | 2 hr*1 | |
| 12 | 2 hr*1 | 2 hr*2 | |
| 13 | | 3 hr*1 | |

The AA running twice was noted as "*2".
order: for C to N

Example 2

Anti-HCV Activity

We next examined the effect of a peptide composed of 14 amino acids DEAQETAVSSHEQD (SEQ ID NO: 1) (designated as DEA), and its derivatives QETAVSSHEQD (SEQ ID NO: 3) (designated as QET) and DEAQETAVSSHEQ (SEQ ID NO: 2) (designated DEA-Q) as prepared in Example 1, in the replication of serum-borne HCV in hADSC and in human primary hepatocytes. Doses of 1, 10 and 100 μg/ml of each peptide was added into the culture of p5 hADSC for 1 h before exposure to HCV(+) serum (genotype 1b). The hADSC were also treated by a control peptide at 100 μg/ml, which was HLA-A11 restricted, Epstein-Barr virus-specific peptide epitope CSSCSSCPLSK (SEQ ID NO: 4)[10]. On day 21 post-infection, the 5'-UTR copy numbers in the supernatant and cell lysates were quantified by qRT-PCR. Results showed that in both the d21 supernatants (FIG. 1A) and cell lysates (FIG. 1B) of HCVser-1b infected hADSC the viral copy numbers were significantly reduced by pretreatment with DEA, DEA-Q or QET peptides, and the inhibitory effect was already noticeable at 1 μg/ml for each peptide. In contrast, pretreatment with control peptide had no effects.

Figure 1:
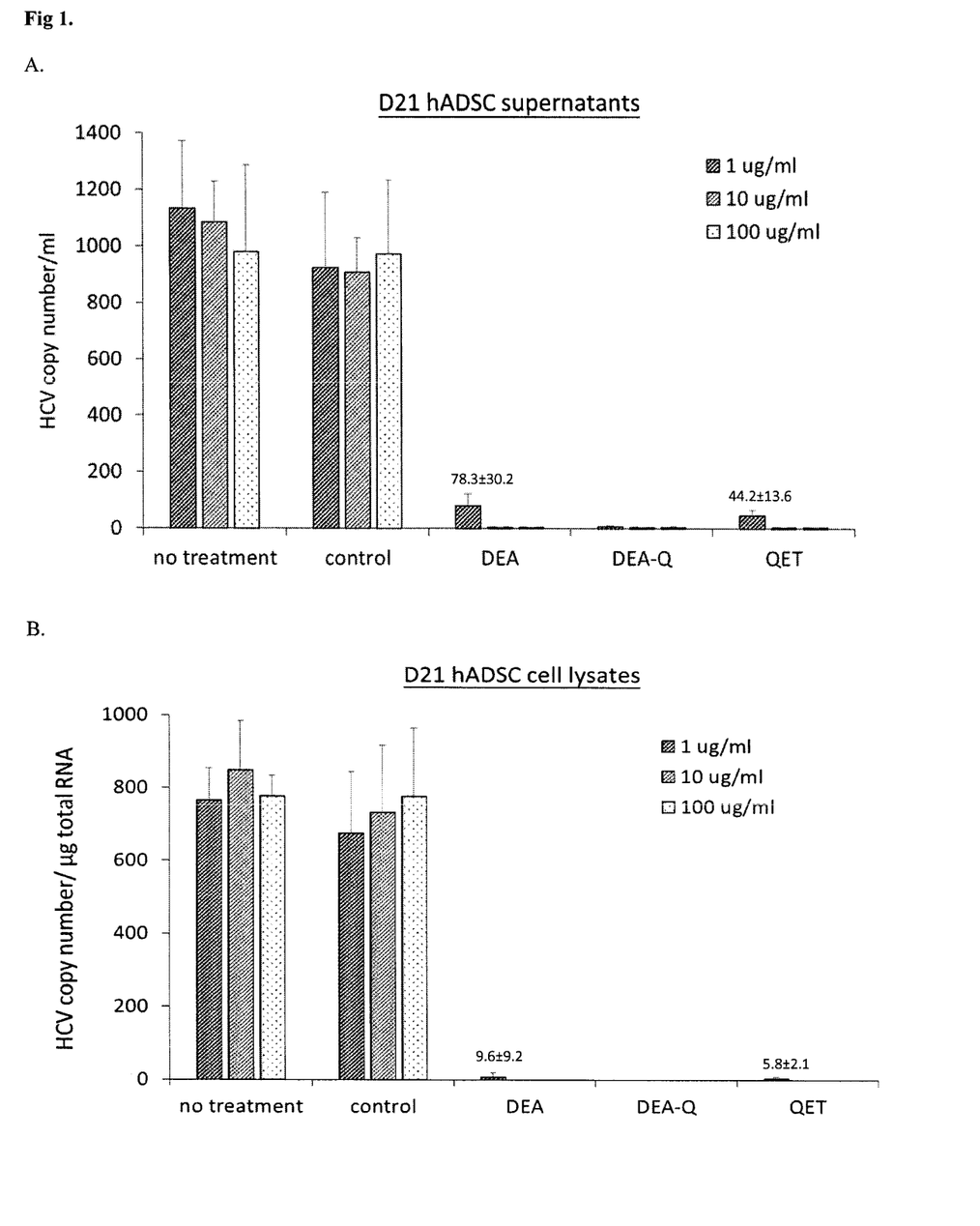

We also examined if these peptides also inhibited HCVser replication in human hepatocytes. Human hepatocytes were isolated from the non-tumoural part away from the lesion, as described[11]. Hepatocytes were left for 3 days to allow attachment onto plastic wells, and subsequently exposed to the HCVser-1b with or without pretreatment with control peptide, DEA, DEA-Q or QET peptide. Five days post-infection, the cellular RNAs were extracted for RT-PCR of 5'-UTR. Results confirmed that as in the case of hADSC, pretreatment with peptides DEA, DEA-Q and QET significantly inhibited the HCVser replication in human hepatocytes, at a concentration as low as 1 μg/ml (FIG. 1C).

In summary, we provide evidence that peptides with sequences of DEAQETAVSSHEQD (SEQ ID NO: 1), DEA-QETAVSSHEQ (SEQ ID NO: 2) and QETAVSSHEQD (SEQ ID NO: 3) possess inhibitory effects over the HCVser replication in both hADSC and primary human hepatocytes. The peptide with sequence of DEAQETAVSSHEQD (SEQ ID NO: 1) is a fragment of rabbit α1-antiproteinase F, and such natural derived product conceivably will lead to a safer profile, and come with a lower production cost.

REFERENCE

1 Lindenbach, B. D. & Rice, C. M. Unravelling hepatitis C virus replication from genome to function. *Nature* 436, 933-938, doi:10.1038/nature04077 (2005).
2 Sheets, W. F. http://www.who.int/mediacentre/factsheets/fs164/en/. (July 2012).
3 Scheel, T. K. & Rice, C. M. Understanding the hepatitis C virus life cycle paves the way for highly effective therapies. *Nature medicine* 19, 837-849, doi:10.1038/nm.3248 (2013).
4 Bartenschlager, R. & Lohmann, V. Novel cell culture systems for the hepatitis C virus. *Antiviral research* 52, 1-17 (2001).
5 Wilson, G. K. & Stamataki, Z. In vitro systems for the study of hepatitis C virus infection. *International journal of hepatology* 2012, 292591, doi:10.1155/2012/292591 (2012).
6 Sheehy, P. et al. In vitro replication models for the hepatitis C virus. *Journal of viral hepatitis* 14, 2-10, doi:10.1111/j.1365-2893.2006.00807.x (2007).
7 Fletcher, N. F. et al. Hepatitis C virus infection of neuroepithelioma cell lines. *Gastroenterology* 139, 1365-1374, doi:10.1053/j.gastro.2010.06.008 (2010).
8 Mercer, D. F. et al. Hepatitis C virus replication in mice with chimeric human livers. *Nature medicine* 7, 927-933, doi:10.1038/90968 (2001).9 Dorner, M. et al. A genetically humanized mouse model for hepatitis C virus infection. *Nature* 474, 208-211, doi:10.1038/nature10168 (2011).
10 Lin, C. L. et al. Immunization with Epstein-Barr Virus (EBV) peptide-pulsed dendritic cells induces functional CD8+ T-cell immunity and may lead to tumor regression in patients with EBV-positive nasopharyngeal carcinoma. *Cancer research* 62, 6952-6958 (2002).
11 Bhogal, R. H. et al. Isolation of primary human hepatocytes from normal and diseased liver tissue: a one hundred liver experience. *PloS one* 6, e18222, doi:10.1371/journal.pone.0018222 (2011).

What is claimed is:

1. A method for reducing HCV viral load in a subject by decreasing the replication of HCV, wherein the method comprises administrating to the subject an effective amount of a peptide comprising amino acid sequence DEAQETAVSSHEQD (SEQ ID NO: 1), QETAVSSHEQD (SEQ ID NO: 3), or DEAQETAVSSHEQ (SEQ ID NO: 2).

2. The method of claim 1, wherein the sequence of the peptide consists essentially of DEAQETAVSSHEQD (SEQ ID NO: 1), QETAVSSHEQD (SEQ ID NO: 3), or DEAQETAVSSHEQ (SEQ ID NO: 2).

3. The method of claim 1, wherein the peptide comprises at least one amino acid addition.

4. The method of claim 3, wherein the amino acid addition is performed at the C-terminal and/or N-terminal.

5. The method of claim 3, wherein the peptide has 1-5 amino acid additions.

6. The method of claim 1, wherein the method further comprises administrating another anti-HCV agent.

7. The method of claim 1, wherein HCV is of genotype 1a, 1b, 2a, or 2b, or genotype 3, or genotype 4.

* * * * *

UNITED STATES PATENT AND TRADEMARK OFFICE
CERTIFICATE OF CORRECTION

| | | |
|---|---|---|
| PATENT NO. | : 11,254,706 B2 | |
| APPLICATION NO. | : 15/566910 | |
| DATED | : February 22, 2022 | |
| INVENTOR(S) | : Chen-Lung Lin | |

It is certified that error appears in the above-identified patent and that said Letters Patent is hereby corrected as shown below:

On the Title Page

Item (54) and in the Specification, Column 1, Lines 1-5, In the title, delete "Peptide And Its Derivatives Capable Of Inhibiting Replication Of Hepatitis V Virus In Human Adipose-Derived Stem Cells And Hepatocytes" and insert --Peptide And Its Derivatives Capable Of Inhibiting Replication Of Hepatitis C Virus In Human Adipose-Derived Stem Cells And Hepatocytes-- therefor.

Signed and Sealed this
Seventh Day of February, 2023

*Katherine Kelly Vidal*

Katherine Kelly Vidal
*Director of the United States Patent and Trademark Office*